United States Patent
Miyazaki

(10) Patent No.: US 10,745,635 B2
(45) Date of Patent: Aug. 18, 2020

(54) LUBRICANT BASE OIL AND LUBRICANT COMPOSITION INCLUDING SAID LUBRICANT BASE OIL

(71) Applicant: KAO CORPORATION, Tokyo (JP)

(72) Inventor: Tatsuya Miyazaki, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/468,839

(22) PCT Filed: Nov. 6, 2017

(86) PCT No.: PCT/JP2017/039944
§ 371 (c)(1),
(2) Date: Jun. 12, 2019

(87) PCT Pub. No.: WO2018/110142
PCT Pub. Date: Jun. 21, 2018

(65) Prior Publication Data
US 2020/0080016 A1  Mar. 12, 2020

(30) Foreign Application Priority Data

Dec. 13, 2016 (JP) .................. 2016-241067
Oct. 31, 2017 (JP) .................. 2017-210267

(51) Int. Cl.
C07C 69/33   (2006.01)
C10M 105/38  (2006.01)
C10N 20/02   (2006.01)

(52) U.S. Cl.
CPC ........... *C10M 105/38* (2013.01); *C07C 69/33* (2013.01); *C10M 2207/2835* (2013.01); *C10N 2020/02* (2013.01)

(58) Field of Classification Search
CPC ........ C10M 105/38; C10M 2207/2835; C10M 2209/1045; C07C 69/33; C07C 69/75; C10N 2220/022; C10N 2230/08; C10N 2220/023; C10N 2220/028; C10N 2230/02; C10N 2230/10; C10N 2230/74
See application file for complete search history.

(56) References Cited

U.S. PATENT DOCUMENTS

| | | | |
|---|---|---|---|
| 4,212,816 A * | 7/1980 | Hentschel | ............ C10M 169/00 508/484 |
| 4,886,614 A | 12/1989 | Yoshimura et al. | |
| 4,889,650 A | 12/1989 | Yoshimura et al. | |
| 5,057,247 A | 10/1991 | Schmid et al. | |
| 5,503,761 A | 4/1996 | Ashcraft, Jr. et al. | |
| 6,884,761 B2 | 4/2005 | Godici et al. | |
| 2010/0130390 A1 | 5/2010 | Tipton et al. | |

FOREIGN PATENT DOCUMENTS

| | | |
|---|---|---|
| EP | 0 003 032 A1 | 7/1979 |
| EP | 0 344 307 B1 | 8/1993 |
| GB | 2 060 624 B | 5/1991 |
| JP | 54-096667 A | 7/1979 |
| JP | 56-115743 A | 9/1981 |
| JP | 62-153393 A | 7/1987 |
| JP | 62-153395 A | 7/1987 |
| JP | 62-283192 A | 12/1987 |
| JP | 63-170337 A | 7/1988 |
| JP | 8-060169 A | 3/1996 |
| JP | 2001-003069 A | 1/2001 |
| JP | 2003-193087 A | 7/2003 |
| JP | 2007-126519 A | 5/2007 |
| JP | 2010-521559 A | 6/2010 |

OTHER PUBLICATIONS

International Preliminary Report on Patentability and English translation of the Written Opinion of the International Searching Authority, dated Jun. 27, 2019, for International Application No. PCT/JP2017/039944.
International Search Report (PCT/ISA/210) issued in PCT/JP2017/039944, dated Dec. 5, 2017.
Bohner et al., "Properties of Polyester Fluids with Desirable Synthetic Lubricant Characteristics", Journal of Chemical and Engineering Data, vol. 7, No. 4, Oct. 1962, pp. 547-553.
European Patent Office Communication and Extended Search Report issued in European Application No. 17882115.3, dated Apr. 23, 2020.

* cited by examiner

*Primary Examiner* — Yevgeny Valenrod
*Assistant Examiner* — Blaine G Doletski
(74) *Attorney, Agent, or Firm* — Birch, Stewart, Kolasch & Birch, LLP

(57) ABSTRACT

This lubricant base oil includes a condensation ester of an alcohol (A) and a carboxylic acid (B), wherein the alcohol (A) contains a polyhydric alcohol represented by general formula (1) (in formula (1), $R^1$-$R^4$ independently represent a hydrogen atom, a methyl group, or a hydroxyl group, and at least two of $R^1$-$R^4$ each represents a hydroxyl group), and the carboxylic acid (B) contains a C4-C8 cycloalkane monocarboxylic acid. The lubricant base oil has excellent heat resistance and lubricating property.

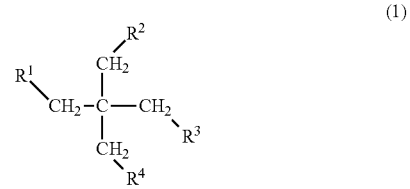

(1)

19 Claims, No Drawings

LUBRICANT BASE OIL AND LUBRICANT COMPOSITION INCLUDING SAID LUBRICANT BASE OIL

TECHNICAL FIELD

The present invention relates to a lubricant base oil, and a lubricant composition including the lubricant base oil. The invention also relates to the use of the lubricant composition, and a lubricating method using the lubricant composition.

BACKGROUND ART

Lubricant oil is used in various fields in which friction decrease is required. In old times, natural fat and oil, petroleum purified products, and others were used. In recent years, however, synthetized lubricant oils have come to be synthesized and used in accordance with articles to be used. In particular, synthesized esters are excellent in thermal stability. Specific examples thereof include organic acid esters, phosphoric acid esters, and silicic acid esters.

Out of the organic acid esters, polyol esters (condensed esters each made from a polyhydric alcohol and a carboxylic acid) are used since the esters 1) are low in pour point and high in viscosity index to be wide in a use-temperature range thereof, 2) are high in flash point and small in evaporation quantity, 3) are excellent in thermal and anti-oxidization stabilities, 4) are good in lubricity, 5) have cleaning and dispersing effects, and 6) have biodegradability. In many fields, in particular, hindered esters are used since the esters are in thermal and anti-oxidization stabilities.

However, in recent years, with developments of industrial techniques, high productivity and operation stability have been constantly required; thus, lubricant oils have come to be required to be higher in endurance and higher in heat resistance.

For example, Patent Document 1 discloses a high-temperature stable lubricant which is economical, is resistant against thermal decomposition, and is smaller in viscosity increment than the existing lubricants. This lubricant is suitable, particularly, for gas turbine engines derived from aircrafts. This lubricant includes a mixed polyol ester in which a carboxylic acid part of this ester includes (a) 2 to 40% by mole of an aromatic carboxylic acid and (b) 60 to 98% by mole of a C5 to C20 aliphatic carboxylic acid, and an alcohol part of the ester includes an aliphatic polyol.

Patent Document 2 discloses a synthesized ester base stock including a reaction product made from pentaerythritol for industries, and a carboxylic acid mixture. The carboxylic acid mixture includes (1) at least one C8-C10 carboxylic acid having 6 or less reactive hydrogen atoms, (2) at least one C5-C7 carboxylic acid having 6 or less reactive hydrogen atoms, and (3) at least one C6-C10 carboxylic acid having 6 or more reactive hydrogen atoms. This synthesized ester base stock is useful for producing turbo oil for aircrafts, and has an effect of restraining the production of deposits in a turbine engine for aircrafts.

Patent Document 3 discloses a synthesized polyol ester which consists substantially of a neutral esterified product made from a specified polyol compound selected as a hydroxyl component, and a specified mono-carboxylic acid and/or a poly-carboxylic acid as one or more acid components, and which is used to produce a temperature-stable lubricant oil dispersant and/or a lubricant grease.

Patent Document 4 discloses a lubricant composition suitable for being used at high temperatures about which the evaporation amount thereof is restrained at high temperatures and the fluidity thereof is kept over a long term. This lubricant composition makes use of a lubricant base oil including 50% or more by mass of a mixture including a hindered ester compound and an aromatic ester compound at a ratio by mass of 5/95 to 95/5.

Patent Document 5 describes an a ester made from an alicyclic carboxylic acid, such as hexahydrobenzoic acid, and a specified polyhydric alcohol. The document discloses that this a ester is used, as a lubricant oil for engines or turbines, in the form of a mixture with another ester or mineral oil lubricant.

PRIOR ART DOCUMENTS

Patent Documents

Patent Document 1: JP-A-2003-193087
Patent Document 2: JP-A-8-60169
Patent Document 3: JP-A-S63-170337
Patent Document 4: JP-A-2007-126519
Patent Document 5: JP-A-S56-115743

SUMMARY OF THE INVENTION

Problems to be Solved by the Invention

As described above, in the prior art, as lubricant oils, various condensed esters have been used. However, in order to improve productivity and operation stability, lubricant oils have been required which are higher in heat resistance, and lubricity.

Thus, an object of the present invention is to provide a lubricant base oil including one or more condensed ester(s) excellent in heat resistance and lubricity; and a lubricant composition including this lubricant base oil.

Means for Solving the Problems

Accordingly, the present invention relates to a lubricant base oil including one or more condensed esters made from one or more alcohols (A) and one or more carboxylic acids (B), wherein the alcohol(s) (A) include(s) a polyhydric alcohol represented by the following general formula (1):

[Formula 1]

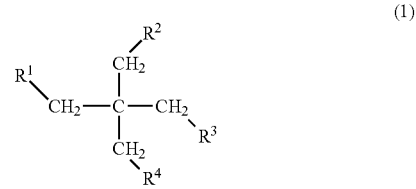

(1)

wherein $R^1$ to $R^4$ each independently represent a hydrogen atom, a methyl group or a hydroxyl group, and further at least two of $R^1$ to $R^4$ are each a hydroxyl group, and the carboxylic acid(s) (B) include(s) a cycloalkane monocarboxylic acid having 4 to 8 (both inclusive) carbon atoms.

The present invention also relates to a lubricant composition, including the above-defined lubricant base oil.

Effect of the Invention

Details of the action mechanism of advantageous effects of the lubricant base oil according to the present invention are partially unclear; however, the mechanism is presumed as described below. However, the invention may not be interpreted with limitation to this action mechanism.

The present invention is a lubricant base oil which includes one or more condensed esters made from one or more alcohols (A) including a polyhydric alcohol represented by the general formula (1), and one or more carboxylic acids (B), and the carboxylic acid(s) (B) includes a cycloalkanecarboxylic acid having 4 to 8 (both inclusive) carbon atoms. According to this form, in the condensed ester (s), an ester chain is formed which is derived from the cycloalkane monocarboxylic acid having 4 to 8 (both inclusive) carbon atoms. This ester chain, which is derived from the cycloalkane monocarboxylic acid, is made chemically stable by effect of a ring strain of its cyclo-ring. The rigidity of the cyclo-ring that is derived from the structure thereof allows a brittle part of the ester(s) to be hardly affected by thermal deterioration. Thus, the ester(s) is/are high in heat resistance to be stably present without being thermally deteriorated even at high temperatures. Consequently, the ester(s) remain(s) in the lubricant base oil or the lubricant composition without being polymerized or volatilized. Such a matter is presumed.

The following is also presumed: the condensed ester (s) having the ester chain derived from the cycloalkane monocarboxylic acid is/are low in crystallinity to be high in fluidity on the basis of an effect of the ring strain of the cyclo-ring and bulkiness effect derived from the structure of the ring; thus, the condensed ester(s) do/does not lower the lubricity of the lubricant base oil, so that the lubricant base oil is excellent in lubricity also.

Furthermore, the following is presumed: when the carboxylic acid(s) (B) include(s) a branched aliphatic acid having a melting point of 25° C. or lower and having 12 to 22 (both inclusive) carbon atoms, an ester chain derived from the branched aliphatic acid is formed in the condensed ester(s); thus, this ester chain exhibits effects of improving the heat resistance and the lubricity in the same manner as the ester chain derived from the cycloalkane monocarboxylic acid, or exhibits the same effects synergistically with the latter ester chain.

Additionally, it is presumed that when the carboxylic acid(s) (B) include(s) an aliphatic acid having 5 to 9 (both inclusive) carbon atoms, the condensed ester(s) can be adjusted into an optimal viscosity, correspondingly to a use of the lubricant base oil.

MODE FOR CARRYING OUT THE INVENTION

The lubricant base oil of the present invention includes one or more condensed esters made from one or more alcohols (A) and one or more carboxylic acids (B); wherein the alcohol(s) (A) include(s) a polyhydric alcohol represented by the following general formula (1):

[Formula 2]

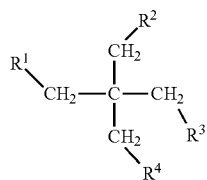

(1)

wherein $R^1$ to $R^4$ each independently represent a hydrogen atom, a methyl group or a hydroxyl group, and further at least two of $R^1$ to $R^4$ are each a hydroxyl group; and the carboxylic acid(s) (B) include(s) a cycloalkane monocarboxylic acid having 4 to 8 (both inclusive) carbon atoms. The lubricant base oil of the present invention denotes compounds which are main components of a lubricant composition, and are blended, together with various lubricant oil additives for giving various functions to the lubricant composition, into the composition to control the viscosity and other physical properties of the lubricant composition.

<Alcohol(s) (A)>

The alcohol(s) (A) include(s) a polyhydric alcohol represented by the general formula (1).

About $R^1$ to $R^4$ in the general formula (1), at least two of $R^1$ to $R^4$ are each a hydroxyl group, and three or more thereof are each preferably a hydroxyl group. Examples of the polyvalent alcohol include pentaerythritol, trimethylolpropane, trimethylolethane, and neopentyl glycol. From the viewpoint of improvements of the condensed alcohol(s) in heat resistance and lubricity, the polyhydric alcohol is preferably pentaerythritol, trimethylolpropane, or neopentyl glycol, more preferably pentaerythritol.

About the alcohol(s) (A), various monohydric alcohols or polyols are each appropriately usable as an alcohol component other than the polyhydric alcohol. The number of carbon atoms in each of the monohydric alcohols is usually from 1 to 24. The carbon chain thereof may be a linear or branched chain. The monohydric alcohol may be saturated or unsaturated. The polyols are each usually a polyol having 2 to 10 valences.

Examples of the polyols include ethylene glycol, diethylene glycol, polyethylene glycol, propylene glycol, dipropylene glycol, polypropylene glycol, 1,3-propanediol, 1,2-propanediol, 1,3-butanediol, 1,4-butanediol, 2-methyl -1,2-propanediol, 2-methyl-1,3-propanediol, 1,2-pentanediol, 1,3-pentanediol, 1,4-pentanediol, 1,5-pentanediol, and other diols; 1,2,4-butanetriol, 1,3,5-pentanetriol, 1,2,6-hexanetriol, and other triol compounds; dipentaerythritol, tripentaerythritol, and other multimers of trimethylolalkanes; glycerol, diglycerol, triglycerol, tetraglycerol, and other polyglycerols; sorbitol, sorbitan, sorbitol glycerin condensates, adonitol, arabitol, xylitol, mannitol, xylose, arabinose, ribose, rhamnose, glucose, fructose, galactose, mannose, sorbose, cellobiose, maltose, isomaltose, trehalose, sucrose, and other saccharides.

<Carboxylic Acid(s) (B)>

The carboxylic acid(s) (B) include(s) a cycloalkane monocarboxylic acid having 4 to 8 (both inclusive) carbon atoms. The cycloalkane monocarboxylic acid may be substituted with an alkyl chain. The alkyl chain may be a linear or branched chain.

The cyclo-ring of the cycloalkane monocarboxylic acid is preferably any one of from 5-membered to 7-membered rings, more preferably a 6-membered ring from the viewpoint of an improvement of the condensed ester(s) in heat resistance.

Examples of the cycloalkane monocarboxylic acid include cyclopropanecarboxylic acid, cyclobutanecarboxylic acid, cyclopentanecarboxylic acid, cyclohexanecarboxylic acid, cycloheptanecarboxylic acid, and methylcyclohexanecarboxylic acid. From the viewpoint of an improvement of the condensed ester(s) in heat resistance, the cycloalkane monocarboxylic acid is preferably cyclopentanecarboxylic acid, cyclohexanecarboxylic acid, cycloheptanecarboxylic acid, or methylcyclohexanecarboxylic acid, more preferably cyclohexanecarboxylic acid, cycloheptanecarboxylic acid, or methylcyclohexanecarboxylic acid, even more preferably cyclohexanecarboxylic acid.

From the viewpoint of improvements of the condensed ester(s) in heat resistance and lubricity, the carboxylic acid(s) (B) include(s) a branched aliphatic acid having a melting point of 25° C. or lower and having 12 to 22 (both inclusive) carbon atoms.

Examples of the branched alkyl aliphatic acid include branched aliphatic acids in each of which a methyl branch has been formed by synthesis using, as a raw material, a linear unsaturated aliphatic acid derived from natural fats and oils, and synthesized aliphatic acids each derived from a polyolefin having a branched chain and yielded by polymerizing 1-butene or any other alkene as a raw material. Any aliphatic acid having a melting point of 25° C. or lower and having 12 to 22 (both inclusive) carbon atoms is usable without any restriction. From the viewpoint of improvements of the condensed ester(s) in heat resistance and lubricity, the melting point is preferably 0° C. or lower.

About the branched aliphatic acid, from the viewpoint of improvements of the condensed ester(s) in heat resistance and lubricity, the number of carbon atoms therein is preferably 15 or more, more preferably 18 or more, and is preferably 20 or less. The number is also preferably from 15 to 20 both inclusive, more preferably from 18 to 20 both inclusive, even more preferably 18.

The carbon chain of the branched aliphatic acid may be unsaturated or saturated. From the viewpoint of the condensed ester(s) in heat resistance, the carbon chain is preferably saturated.

Examples of the branched aliphatic acid include 13-methyltetradecanoic acid, 12-methyltetradecanoic acid, 15-methylhexadecanoic acid, 14-methylhexadecanoic acid, 10-methylhexadecanoic acid, 2-hexyldecanoic acid, isopalmitic acid, isostearic acid, isoarachic acid, and phytanic acid. From the viewpoint of improvements of the condensed ester(s) in heat resistance and lubricity, the branched aliphatic acid is preferably 2-hexyldecanoic acid, isopalmitic acid, isostearic acid, or isoarachic acid, more preferably isostearic acid or isopalmitic acid.

In order to lower the condensed ester(s) in viscosity to lower the lubricant composition in torque, and make the filling-work of the lubricant composition efficient, the carboxylic acid(s) (B) preferably include(s) an aliphatic acid having 5 to 9 (both inclusive) carbon atoms.

Specific examples of the aliphatic acid having 5 to 9 (both inclusive) carbon atoms include valeric acid, 2-methylvaleric acid, 4-methylvaleric acid, n-hexanoic acid, 2-methylhexanoic acid, 5-methylhexanoic acid, 4,4-dimethylpentanoic acid, n-heptanoic acid, 2-methylheptanoic acid, 2-ethylhexanoic acid, 2,2-dimethylhexanoic acid, n-octanoic acid, 3,5,5-trimethylhexanoic acid, and n-nonanoic acid. From the viewpoint of the heat resistance, more preferred are linear valeric acid, n-hexanoic acid, n-heptanoic acid, n-octanoic acid and n-nonanoic acid, and more preferred is n-heptanoic acid.

For the carboxylic acid(s) (B), as a carboxylic acid other than the cycloalkane monocarboxylic acid, the branched aliphatic acid and the aliphatic acid having 5 to 9 (both inclusive) carbon atoms, a carboxylic acid that may be of various types (hereinafter referred to as a different carboxylic acid compound) may be appropriately used. Examples of the different carboxylic acid include benzoic acid, naphthoic acid, and other aromatic carboxylic acids; and capric acid, lauric acid, myristic acid, palmitic acid, and stearic acid.

Hereinafter, a description will be made about the blend amount of each of the components in the present invention.

In the alcohol(s) (A), the proportion of the polyhydric alcohol represented by the general formula (1) is preferably 80% or more by mole, more preferably 90% or more by mole, even more preferably 95% or more by mole, even more preferably 98% or more by mole, even more preferably 100% by mole.

In the carboxylic acid(s) (B), the proportion of the cycloalkane monocarboxylic acid is preferably from 10 to 70% by mole both inclusive to improve the condensed ester(s) in heat resistance and lubricity. In the carboxylic acid(s) (B), the proportion of the cycloalkane monocarboxylic acid is preferably 20% or more by mole to improve the condensed ester(s) in heat resistance, and the proportion is more preferably 60% or less by mole, even more preferably 55% or less by mole to improve the condensed ester(s) in lubricity.

In the carboxylic acid(s) (B), the proportion of the branched aliphatic acid may be 0% by mole to lower the condensed ester(s) in pour point. The proportion is preferably 10% or more by mole, more preferably 20% or more by mole to improve the condensed ester(s) in heat resistance and heighten the ester(s) in kinetic viscosity. The proportion is preferably 50% or less by mole, more preferably 40% or less by mole to lower the pour point of the condensed ester(s) to lower the kinetic viscosity thereof.

In the carboxylic acid(s) (B), the total proportion of the cycloalkane monocarboxylic acid and the branched aliphatic acid is preferably from 10 to 70% by mole both inclusive to improve the condensed ester(s) in heat resistance and lubricity. In the carboxylic acid(s) (B), this total proportion is more preferably 20% or more by mole, even more preferably 30% or more by mole to improve the ester compound(s) in lubricity. The proportion is more preferably 60% or less by mole, even more preferably 50% or less by mole to lower the viscosity of the ester compound(s) to realize a decrease in the torque of the lubricant composition, and to make the filling-work thereof efficient.

In the carboxylic acid(s) (B), the ratio by mole of the cycloalkane monocarboxylic acid to the branched aliphatic acid (the ratio of the cycloalkane monocarboxylic acid/the branched aliphatic acid) is preferably from 0.05 to 0.7 both inclusive to improve the condensed ester(s) in heat resistance and lubricity. The ratio is more preferably 0.1 or more, even more preferably 0.2 or more to improve the condensed ester(s) in heat resistance and lower the ester(s) in pour point. The ratio is more preferably 0.6 or less, even more preferably 0.5 or less to improve the condensed ester(s) in lubricity.

In the carboxylic acid(s) (B), the proportion of the aliphatic acid having 5 to 9 (both inclusive) carbon atoms may be 0% by mole to improve the condensed ester(s) in heat resistance. The proportion is from 10 to 90% by mole both inclusive to lower the viscosity of the condensed ester(s) to realize a decrease in the torque of the lubricant composition, and to make the filling-work thereof efficient. In the carboxylic acid(s) (B), the proportion of the aliphatic acid having 5 to 9 (both inclusive) carbon atoms is more preferably 20% or more by mole, even more preferably 30% or more by mole, even more preferably 40% or mole by mole, even more preferably 50% or more by mole, even more preferably 60% or more by mole to lower the viscosity of the condensed ester(s) to realize a decrease in the torque of the lubricant composition, and to make the filling-work thereof efficient. In the carboxylic acid(s) (B), the proportion of the aliphatic acid having 5 to 9 (both inclusive) carbon atoms is preferably 80% or less by mole, more preferably 70% or less by mole, even more preferably 60% or less by mole, even more preferably 50% or less by mole, even more preferably 40% or less by mole, even more preferably 30% or less by mole to improve the condensed ester(s) in heat resistance.

In the carboxylic acid(s) (B), the ratio by mole of the cycloalkane monocarboxylic acid to the aliphatic acid having 5 to 9 (both inclusive) carbon atoms (the ratio of the cycloalkane monocarboxylic acid/the aliphatic acid having 5 to 9 (both inclusive) carbon atoms) is preferably from 0.04 to 0.7 both inclusive to improve the condensed ester(s) in heat resistance and lubricity. The ratio is more preferably 0.08 or more, even more preferably 0.1 or more to improve the heat resistance of the condensed ester(s) and lower the pour point thereof. The ratio is more preferably 0.3 or less, even more preferably 0.2 or less to improve the condensed ester(s) in lubricity.

In the carboxylic acid(s) (B), the total proportion of the cycloalkane monocarboxylic acid, the branched aliphatic acid, and the aliphatic acid having 5 to 9 (both inclusive) carbon atoms is preferably 80% or more by mole, more preferably 90% or more by mole, even more preferably 95% or more by mole, even more preferably 98% or more by mole, even more preferably 100% by mole to improve the condensed ester(s) in heat resistance and lubricity.

In the lubricant base oil, the proportion of the condensed ester(s) is preferably from 50 to 100% by mass both inclusive, more preferably 60% or more by mass, even more preferably 70% or more by mass, even more preferably 80% or more by mass, even more preferably 90% or more by mass, even more preferably 100% by mass to improve the condensed ester(s) in heat resistance and lubricity.

<Method for Preparing the Condensed Ester(s)>

The condensed ester(s) can be prepared by subjecting one or more alcohols (A) including a polyhydric alcohol represented by the general formula (1) and one or more carboxylic acids including a cycloalkane monocarboxylic acid (B) having 4 to 8 (both inclusive) carbon atoms to esterification reaction in a known way.

In the reaction between the alcohol(s) (A) and the carboxylic acid(s) (B), about the ratio by equivalent between the two, usually, the amount of carboxyl groups of one or more carboxylic acid components in the carboxylic acid(s) (B) is preferably from 1.05 to 1.5 equivalents, more preferably from 1.1 to 1.3 equivalents per equivalent of hydroxyl groups of one or more alcohol components in the alcohol(s) (A) to promote the esterification reaction. When the proportion of the carboxyl groups of the carboxylic acid component(s) in the carboxylic acid(s) (B) is made high, the reactivity between the alcohol component(s) and the carboxylic acid component(s) becomes good. However, after the end of the reaction, an excessive fraction of the carboxylic acid(s) (B) needs to be removed. Examples of a method for the removal include reduced-pressure distillation, steaming, and adsorption and removal using an adsorbent.

About the condensed ester(s) in the present invention, the 40° C. kinetic viscosity thereof, which will be detailed later, is preferably 5 mm²/s or more, more preferably 10 mm²/s or more, and is preferably 200 mm²/s or less, more preferably 100 mm²/s or less to keep the lubricity of the lubricant base oil certainly at low temperatures. Moreover, about the condensed ester(s) in the invention, the 100° C. kinetic viscosity thereof, which will be detailed later, is preferably 2 mm²/s or more, more preferably 5 mm²/s or more, and is preferably 20 mm²/s or less, more preferably 15 mm²/s or less to keep the lubricity of the lubricant base oil certainly at high temperatures.

Furthermore, about the condensed ester(s) in the present invention, the pour point thereof, which will be detailed later, is preferably −20° C. or lower, more preferably −30° C. or lower, even more preferably −40° C. or lower, even more preferably −50° C. or lower to keep the lubricity of the lubricant base oil certainly at low temperatures.

<Lubricant Composition>

The lubricant composition of the present invention includes the above-defined lubricant base oil.

As required, other additives may be blended into the lubricant composition as far as the advantageous effects of the present invention are not damaged. Examples of the other additives include a detergent, a dispersant, an antioxidant, an oiliness improver, an antiwear agent, an extreme pressure agent, a rust inhibitor, a corrosion inhibitor, a metal deactivator, a viscosity index improver, a pour point depressant, an antifoaming agent, an emulsifier, a demulsifier, an anti-mold agent, and a solid lubricant.

The total blend amount of the other additives is usually 10 parts or less by mass, preferably 5 parts or less by mass for 100 parts by mass of the lubricant composition.

The lubricant composition of the present invention is usable for gasoline engine oil, diesel engine oil, marine engine oil, and other combustion lubricant oils; and gear oil, automatic transmission oil, hydraulic oil, fire-resistant hydraulic fluid, refrigerator oil, compressor oil, vacuum pump oil, bearing oil, insulating oil, turbine oil, sliding surface oil, rock drill oil, metal working oil, plastic working oil, heat treatment oil, grease, and other non-combustion type lubricant oils. The lubricant composition of the present invention is used in particular preferably as any one of the non-combustion type lubricant oils. The lubricant composition of the present invention is also usable for sliding parts, such as rotating and sliding parts as a sliding bearing, plane sliding parts such as a thrust bearing, and sliding parts such as a spline; and is usable for a method for lubricating a spline section of a clutch disc, a shaft and a gear-inside-diameter bearing section of a transmission, a spline section of a hub-sleeve, a section supported by a metal in each section, and a spline section of a change operating system.

In connection with the above-mentioned embodiments, the present document DESCRIPTION discloses the following lubricant base oil, and lubricant composition including the lubricant base oil:

<1> A lubricant base oil, including one or more condensed esters made from one or more alcohols (A) and one or more carboxylic acids (B), wherein the alcohol(s) (A) include(s) a polyhydric alcohol represented by the following general formula (1):

[Formula 3]

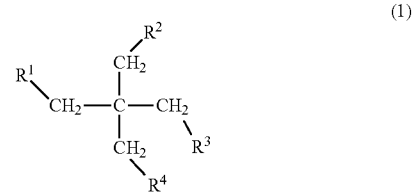

(1)

wherein $R^1$ to $R^4$ each independently represent a hydrogen atom, a methyl group or a hydroxyl group, and further at least two of $R^1$ to $R^4$ are each a hydroxyl group; and the carboxylic acid(s) (B) include(s) a cycloalkane monocarboxylic acid having 4 to 8 (both inclusive) carbon atoms.

<2> The lubricant base oil according to item <1>, wherein about $R^1$ to $R^4$ in the general formula (1), at least two of $R^1$ to $R^4$ are each a hydroxyl group, and three or more thereof are each preferably a hydroxyl group.

<3> The lubricant base oil according to item <1> or <2>, wherein the polyhydric alcohol is preferably pentaerythritol, trimethylolpropane, trimethylolethane, or neopentyl glycol, more preferably pentaerythritol, trimethylolpropane, or neopentyl glycol, even more preferably pentaerythritol.

<4> The lubricant base oil according to any one of items <1> to <3>, wherein the cyclo-ring of the cycloalkane monocarboxylic acid is any one of from 5-membered to 7-membered rings, more preferably a 6-membered ring.

<5> The lubricant base oil according to any one of items <1> to <4>, wherein the cycloalkane monocarboxylic acid is preferably cyclopropanecarboxylic acid, cyclobutanecarboxylic acid, cyclopentanecarboxylic acid, cyclohexanecarboxylic acid, cycloheptanecarboxylic acid, or methylcyclohexanecarboxylic acid; more preferably cyclopentanecarboxylic acid, cyclohexanecarboxylic acid, cyclobutanecarboxylic acid, or methylcyclohexanecarboxylic acid; even more preferably cyclohexanecarboxylic acid, cycloheptanecarboxylic acid, or methylcyclohexanecarboxylic acid; even more preferably cyclohexanecarboxylic acid.

<6> The lubricant base oil according to any one of items <1> to <5>, wherein the carboxylic acid(s) (B) include(s) a branched aliphatic acid having a melting point of 25° C. or lower, and having 12 to 22 (both inclusive) carbon atoms.

<7> The lubricant base oil according to item <6>, wherein the melting point is preferably 0° C. or lower.

<8> The lubricant base oil according to item <6> or <7>, wherein about the branched aliphatic acid, the number of carbon atoms therein is preferably 15 or more, more preferably 18 or more, and is preferably 20 or less, more preferably from 15 to 20 both inclusive, even more preferably from 18 to 20 both inclusive, even more preferably 18.

<9> The lubricant base oil according to any one of items <6> to <8>, wherein the branched aliphatic acid preferably has a saturated carbon chain.

<10> The lubricant base oil according to any one of items <6> to <9>, wherein the branched aliphatic acid is preferably 13-methyltetradecanoic acid, 12-methyltetradecanoic acid, 15-methylhexadecanoic acid, 14-methylhexadecanoic acid, 10-methylhexadecanoic acid, 2-hexyldecanoic acid, isopalmitic acid, isostearic acid, isoarachic acid, or phytanic acid; more preferably 2-hexyldecanoic acid, isopalmitic acid, isostearic acid, or isoarachic acid; even more preferably isostearic acid, or isopalmitic acid.

<11> The lubricant base oil according to any one of items <1> to <10>, wherein the carboxylic acid(s) (B) include(s) an aliphatic acid having 5 to 9 (both inclusive) carbon atoms.

<12> The lubricant base oil according to item <11>, wherein the aliphatic acid having 5 to 9 (both inclusive) carbon atoms is preferably valeric acid, 2-methylvaleric acid, 4-methylvaleric acid, n-hexanoic acid, 2-methylhexanoic acid, 5-methylhexanoic acid, 4,4-dimethylpentanoic acid, n-heptanoic acid, 2-methylheptanoic acid, 2-ethylhexanoic acid, 2,2-dimethylhexanoic acid, n-octanoic acid, 3,5,5-trimethylhexanoic acid, or n-nonanoic acid; more preferably linear valeric acid, n-hexanoic acid, n-heptanoic acid, n-octanoic acid or n-nonanoic acid; even more preferably n-heptanoic acid.

<13> The lubricant base oil according to any one of items <1> to <12>, wherein the proportion of the polyhydric alcohol represented by the general formula (1) in the alcohol(s) (A) is preferably 80% or more by mole, more preferably 90% or more by mole, more preferably 95% or more by mole, even more preferably 98% or more by mole, even more preferably 100% by mole.

<14> The lubricant base oil according to any one of items <1> to <13>, wherein the proportion of the cycloalkane monocarboxylic acid in the carboxylic acid(s) (B) is preferably from 10 to 70% by mole both inclusive, more preferably 20% or more by mole, and is more preferably 60% or less by mole, even more preferably 55% or less by mole.

<15> The lubricant base oil according to any one of items <6> to <14>, wherein the proportion of the branched aliphatic acid in the carboxylic acid(s) (B) may be 0% by mole, and is preferably 10% or more by mole, more preferably 20% or more by mole, and is preferably 50% or less by mole, more preferably 40% or less by mole.

<16> The lubricant base oil according to any one of items <6> to <15>, wherein the total proportion of the cycloalkane monocarboxylic acid and the branched aliphatic acid in the carboxylic acid(s) (B) is preferably from 10 to 70% by mole both inclusive, more preferably 20% or more by mole, even more preferably 30% or more by mole, and is more preferably 60% or less by mole, more preferably 50% or less by mole.

<17> The lubricant base oil according to any one of items <6> to <16>, wherein in the carboxylic acid(s) (B), the ratio by mole of the cycloalkane monocarboxylic acid to the branched aliphatic acid (the ratio of the cycloalkane monocarboxylic acid/the branched aliphatic acid) is preferably from 0.05 to 0.7 both inclusive, more preferably 0.1 or more, even more preferably 0.2 or more, and is more preferably 0.6 or less, even more preferably 0.5 or less.

<18> The lubricant base oil according to any one of items <11> to <17>, wherein in the carboxylic acid(s) (B), the proportion of the aliphatic acid having 5 to 9 (both inclusive) carbon atoms may be 0% or more, and is preferably from 10 to 90% by mole both inclusive, more preferably 20% or more by mole, even more preferably 30% or mole by mole, even more preferably 40% or more by mole, even more preferably 50% or more by mole, 60% or more by mole, and is preferably 80% or less by mole, mote preferably 70% or less by mole, even more preferably 60% or less by mole, even more preferably 50% or less by mole, even more preferably 40% or less by mole, even more preferably 30% or less by mole.

<19> The lubricant base oil according to any one of items <11> to <18>, wherein in the carboxylic acid(s) (B), the ratio by mole of the cycloalkane monocarboxylic acid to the aliphatic acid having 5 to 9 (both inclusive) carbon atoms (the ratio of the cycloalkane monocarboxylic acid/the aliphatic acid having 5 to 9 (both inclusive) carbon atoms) is preferably from 0.04 to 0.7 both inclusive, more preferably 0.08 or more, even more preferably 0.1 or more, and is more preferably 0.3 or less, even more preferably 0.2 or less.

<20> The lubricant base oil according to any one of items <11> to <19>, wherein in the carboxylic acid(s) (B), the total proportion of the cycloalkane monocarboxylic acid, the branched aliphatic acid and the aliphatic acid having 5 to 9 (both inclusive) carbon atoms is preferably 80% or more by mole, more preferably 90% or more by mole, even more preferably 95% or more by mole, even more preferably 98% or more by mole, even more preferably 100% by mole.

<21> The lubricant base oil according to any one of items <1> to <20>, wherein the proportion by mass of the ester compound(s) is preferably from 50 to 100% by mass both inclusive, more preferably 60% or more by mass, even more preferably 70% or more by mass, even more preferably 80% or more by mass, even more preferably 90% or more by mass, even more preferably 100% by mass.

<22> A lubricant composition including the lubricant base oil recited in any one of items <1> to <21>.

<23> Use of the lubricant composition recited in item <22> for a sliding part.

<24> A lubricating method, using the lubricant composition recited in item <22>.

EXAMPLES

Hereinafter, the present invention will be described in more detail by way of working examples thereof.

However, the invention is not limited only to these working examples.

Example 1

<Preparation of Condensed Ester(s)>

Into a 1-L four-necked flask equipped with a stirrer, a thermometer, a nitrogen-blowing tube and a condenser were added 315.5 g of n-heptanoic acid (heptanoic acid, manufactured by Tokyo Chemical Industry Co., Ltd.), 275.8 g of isostearic acid (Prisorine 3501, manufactured by Croda Japan K.K.; melting point: 0° C. or lower) and 62.1 g of cyclohexanecarboxylic acid (manufactured by Tokyo Chemical Industry Co., Ltd.) as carboxylic acids (B), and 110 g of pentaerythritol (manufactured by Tokyo Chemical Industry Co., Ltd.) as an alcohol (A). The addition amount of the carboxylic acids (B) was adjusted to set the amount of all carboxyl groups of the carboxylic acids (B) to 1.2 equivalents per equivalent of hydroxyl groups of the alcohol (A).

Next, nitrogen gas was blown into the flask. While the reaction system was stirred, the temperature thereof was raised to 250° C. The system was kept at 250° C. for 18 hours. The condenser was used to remove water distilled off therefrom to the outside of the flask. After the end of the reaction, an excess of the carboxylic acid components was distilled off under a reduced pressure of 0.13 kPa. Under the reduced pressure of 0.13 kPa, the system was subjected to steaming for one hour to cause remaining fractions of the carboxylic acid components to be adsorbed on an adsorbent (trade name: KYOWAAD 500SH, manufactured by Kyowa Chemical Industry Co., Ltd.). Thereafter, the production system was filtrated to yield condensed esters in Example 1. About the resultant condensed esters, evaluations described below were made. The evaluation results are shown in Table 1.

<Evaluation of Heat Resistance>

In an evaluation of the heat resistance of the sample, a differential thermo-gravity simultaneously-measuring device (trade name: TG/DTA 6200, manufactured by Seiko Instruments Inc.) was used to raise the temperature of the sample from 35° C. to 550° C. at 10° C./minute in a 250-mL/minute atmosphere of nitrogen and air. Under conditions that the sample was kept at the temperature of 550° C. for 10 minutes, the thermal response of the condensed esters was measured, and the residual percentage (% by mass) thereof was calculated out in accordance with an expression described below. It is demonstrated that as the residual percentage is larger, the heat resistance is better.

Expression: residual percentage (% by mass)="the mass of the sample at 350° C."/"the mass thereof at 35° C."×100

<Evaluation of Kinetic Viscosity>

In an evaluation of the kinetic viscosity of the sample, the 40° C. kinetic viscosity and the 100° C. kinetic viscosity (mm$^2$/s) thereof were measured, using a Stabinger kinetic viscometer (trade name: SVM3000, manufactured by Anton Paar GmbH) satisfying a precision required in ASTM D7042.

<Evaluation of Pour Point>

In an evaluation of the pour point of the sample, the pour point (° C.) was measured by a measuring method according to JIS K2269.

Examples 2 to 7, and Comparative Examples 1 and 2

In each of the examples, condensed esters were prepared and evaluated in the same way as in Example 1 except that the species and the blend amounts of the individual raw materials were changed as shown in Table 1. The evaluation results are shown in Table 1. Neopentyl glycol used therein was 2,2-dimethyl-1,3-propanediol (manufactured by Tokyo Chemical Industry Co., Ltd.).

Comparative Examples 3 and 4

In each of the examples, condensed esters were prepared and evaluated in the same way as in Example 1 except that the species and the blend amounts of the individual raw materials were changed as shown in Table 1. The evaluation results are shown in Table 1. Dipropylene glycol used therein was manufactured by Nacalai Tesque, Inc., and polyethylene glycol 400 used therein was manufactured by Tokyo Chemical Industry Co., Ltd.

TABLE 1

| | | Charged components | | | | | |
|---|---|---|---|---|---|---|---|
| | | Raw materials B | | | | | |
| | | % by mole | | | | % by mass | |
| | Raw material A | n-Heptanoic acid | Isostearic acid | Cyclohexane carboxylic acid | Stearic acid | n-Heptanoic acid | Isostearic acid |
| Example 1 | Pentaerythritol | 62.5 | 25.0 | 12.5 | — | 48.3 | 42.2 |
| Example 2 | Pentaerythritol | 60.0 | 30.0 | 10.0 | — | 44.3 | 48.4 |
| Example 3 | Pentaerythritol | 57.5 | 35.0 | 7.5 | — | 40.7 | 54.1 |
| Example 4 | Pentaerythritol | 55.0 | 40.0 | 5.0 | — | 37.3 | 59.3 |
| Example 5 | Pentaerythritol | 52.5 | 45.0 | 2.5 | — | 34.2 | 64.2 |
| Example 6 | Pentaerythritol | 37.5 | 37.5 | 25.0 | — | 26.0 | 56.9 |
| Example 7 | Neopentyl glycol | 50.0 | — | 50.0 | — | 50.4 | — |

TABLE 1-continued

| | | Charged components Raw materials A | | | | | |
|---|---|---|---|---|---|---|---|
| Comparative Example 1 | Pentaerythritol | 100 | — | — | — | 100 | — |
| Comparative Example 2 | Neopentyl glycol | 100 | — | — | — | 100 | — |
| Comparative Example 3 | Dipropylene glycol | — | — | 98 | 2 | — | — |
| Comparative Example 4 | Polyethylene glycol 400 | — | — | 100 | — | — | — |

| | Charged components Raw materials B | | Evaluations | | | |
|---|---|---|---|---|---|---|
| | % by mass | | | 40° C. | 100° C. | |
| | Cyclohexane carboxylic acid | Stearic acid | Residual percentage (% by mass) | Kinetic viscosity (mm²/s) | Kinetic viscosity (mm²/s) | Pour point (° C.) |
| Example 1 | 9.5 | — | 73.4 | 50.70 | 8.33 | −44 |
| Example 2 | 7.3 | — | 86.7 | 54.79 | 8.85 | −41 |
| Example 3 | 5.2 | — | 80.7 | 58.73 | 9.36 | −39 |
| Example 4 | 3.4 | — | 82.6 | 63.29 | 9.92 | −37 |
| Example 5 | 1.6 | — | 80.9 | 68.96 | 10.63 | −34 |
| Example 6 | 17.1 | — | 87.1 | 95.49 | 12.48 | −45 |
| Example 7 | 49.6 | — | 75.2 | 10.08 | 2.68 | −50> |
| Comparative Example 1 | — | — | 55.4 | 22.28 | 4.74 | −35 |
| Comparative Example 2 | — | — | 67.8 | 5.66 | 1.90 | −50> |
| Comparative Example 3 | 95.7 | 4.3 | 2.1 | 23.34 | 4.37 | −34 |
| Comparative Example 4 | 100 | — | 12.2 | 42.98 | 8.33 | −40 |

The invention claimed is:

1. A lubricant base oil comprising one or more condensed esters made from one or more alcohols (A) and one or more carboxylic acids (B), wherein the alcohol(s) (A) comprise(s) a polyhydric alcohol represented by a general formula (1):

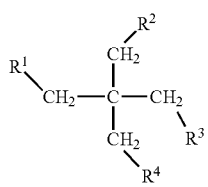

(1)

wherein $R^1$ to $R^4$ each independently represent a hydrogen atom, a methyl group or a hydroxyl group, and further at least two of $R^1$ to $R^4$ are each a hydroxyl group, and the carboxylic acid(s) (B) comprise(s) a cycloalkane monocarboxylic acid having 4 to 8 (both inclusive) carbon atoms, and a branched aliphatic acid having a melting point of 25° C. or lower and having 12 to 22 (both inclusive) carbon atoms, wherein a ratio by mole of the cycloalkane monocarboxylic acid to the branched aliphatic acid (the ratio of the cycloalkane monocarboxylic acid/the branched aliphatic acid) is from 0.05 to 0.7 both inclusive.

2. The lubricant base oil according to claim 1, wherein the cycloalkane monocarboxylic acid is cyclohexanecarboxylic acid, and the branched aliphatic acid is isostearic acid.

3. The lubricant base oil according to claim 1, wherein the carboxylic acid(s) (B) comprise(s) an aliphatic acid having 5 to 9 (both inclusive) carbon atoms.

4. The lubricant base oil according to claim 3, wherein the aliphatic acid having 5 to 9 (both inclusive) carbon atoms is n-heptanoic acid.

5. The lubricant base oil according to claim 1, wherein a proportion of the cycloalkane monocarboxylic acid in the carboxylic acid(s) (B) is from 10 to 70% by mole both inclusive.

6. The lubricant base oil according to claim 1, wherein a total proportion of the cycloalkane monocarboxylic acid and the branched aliphatic acid in the carboxylic acid(s) (B) is from 10 to 70% by mole both inclusive.

7. The lubricant base oil according to claim 3, wherein a proportion of the aliphatic acid having 5 to 9 (both inclusive) carbon atoms in the carboxylic acid(s) (B) is from 10 to 90% by mole both inclusive.

8. The lubricant base oil according to claim 1, wherein a proportion of the condensed ester(s) in the lubricant base oil is from 50 to 100% by mass both inclusive.

9. A lubricant composition, comprising the lubricant base oil recited in claim 1.

10. The lubricant base oil according to claim 3, wherein a ratio by mole of the cycloalkane monocarboxylic acid to the aliphatic acid having 5 to 9 (both inclusive) carbon atoms (the ratio of the cycloalkane monocarboxylic acid/the aliphatic acid having 5 to 9 (both inclusive) carbon atoms) is from 0.04 to 0.7 both inclusive.

11. The lubricant base oil according to claim 1, wherein the pour point of the condensed ester(s) measured by a measuring method according to JIS K2269 is −40° C. or lower.

12. The lubricant base oil according to claim 1, wherein the alcohol (A) is one or more selected from the group consisting of pentaerythritol, trimethylolpropane, and neopentyl glycol.

13. The lubricant base oil according to claim 1, wherein the cyclo-ring of the cycloalkane monocarboxylic acid is any one of from 5-membered to 7-membered rings.

14. The lubricant base oil according to claim 1, wherein the branched aliphatic acid has 15 to 20 (both inclusive) carbon atoms.

15. The lubricant base oil according to claim 1, wherein a proportion of the branched aliphatic acid in the carboxylic acid(s) (B) is from 20 to 50% by mole both inclusive.

16. The lubricant base oil according to claim 3, wherein a proportion of the aliphatic acid having 5 to 9 (both inclusive) carbon atoms in the carboxylic acid(s) (B) is from 30 to 70% by mole both inclusive.

17. The lubricant base oil according to claim 3, wherein a total proportion of the cycloalkane monocarboxylic acid, the branched aliphatic acid, and the aliphatic acid having 5 to 9 (both inclusive) carbon atoms is 95% or more by mole.

18. The lubricant base oil according to claim 1, wherein the 40° C. kinetic viscosity of the condensed ester(s) is from 10 to 100 $mm^2/s$ both inclusive, and the 100° C. kinetic viscosity of the condensed ester(s) is from 5 to 15 $mm^2/s$ both inclusive.

19. The lubricant base oil according to claim 1, wherein a proportion of the cycloalkane monocarboxylic acid in the carboxylic acid(s) (B) is from 2.5 to 55% by mole both inclusive.

\* \* \* \* \*